(12) United States Patent
Deisseroth

(10) Patent No.: US 10,130,667 B1
(45) Date of Patent: Nov. 20, 2018

(54) TAA/ECDCD40L ONCOLYTIC VIRUS

(71) Applicant: Albert B. Deisseroth, Potomac, MD (US)

(72) Inventor: Albert B. Deisseroth, Potomac, MD (US)

(73) Assignee: MicroVAX, LLC, Warrenton, VA (US)

( * ) Notice: Subject to any disclaimer, the term of this patent is extended or adjusted under 35 U.S.C. 154(b) by 33 days.

(21) Appl. No.: 15/130,041

(22) Filed: Apr. 15, 2016

Related U.S. Application Data

(62) Division of application No. 14/163,039, filed on Jan. 24, 2014, now abandoned.

(60) Provisional application No. 61/757,311, filed on Jan. 28, 2013.

(51) Int. Cl.
| | |
|---|---|
| *A61K 35/761* | (2015.01) |
| *A61K 48/00* | (2006.01) |
| *C12N 7/00* | (2006.01) |
| *A61K 38/16* | (2006.01) |
| *A61K 9/00* | (2006.01) |
| *A61K 31/513* | (2006.01) |
| *A61K 38/50* | (2006.01) |
| *A61K 39/00* | (2006.01) |
| *C12N 15/861* | (2006.01) |
| *C07K 14/005* | (2006.01) |

(52) U.S. Cl.
CPC .......... *A61K 35/761* (2013.01); *A61K 9/0019* (2013.01); *A61K 31/513* (2013.01); *A61K 38/162* (2013.01); *A61K 38/50* (2013.01); *A61K 39/0011* (2013.01); *A61K 48/0058* (2013.01); *C12N 7/00* (2013.01); *A61K 2039/53* (2013.01); *C07K 14/005* (2013.01); *C12N 15/861* (2013.01); *C12N 2710/00011* (2013.01); *C12N 2710/10011* (2013.01); *C12N 2710/10032* (2013.01); *C12N 2710/10034* (2013.01); *C12N 2710/10041* (2013.01); *C12N 2710/10332* (2013.01); *C12N 2710/10343* (2013.01); *C12Y 305/04001* (2013.01)

(58) Field of Classification Search
CPC .............. A61K 2300/00; A61K 38/177; A61K 39/0011; A61K 39/39558; A61K 38/00; A61K 48/005; A61K 2039/54; A61K 39/00; A61K 48/0058; A61K 2039/5154; A61K 2039/53; A61K 35/76; A61K 39/12; A61K 35/761; C07K 14/7051; C07K 2319/33; C07K 14/005; C07K 14/705; C07K 14/075; C12N 15/86; C12N 7/00; C12N 15/861; C12N 2710/10032; C12N 2710/10011; C12N 2710/10041; C12N 2710/10034
See application file for complete search history.

(56) References Cited

U.S. PATENT DOCUMENTS

2009/0280552 A1* 11/2009 Freytag ................ C12N 9/1211
435/194

OTHER PUBLICATIONS

Rautio J, Kumpulainen H, Heimbach T, Oliyai R, Oh D, Järvinen T, Savolainen J. Prodrugs: design and clinical applications. Nat Rev Drug Discov. Mar. 2008;7(3):255-70. Review. Erratum in: Nat Rev Drug Discov. Mar. 2008;7(3):272.*

Deisseroth A, Tang Y, Zhang L, Akbulut H, Habib N. TAA/ecdCD40L adenoviral prime-protein boost vaccine for cancer and infectious diseases. Cancer Gene Ther. Feb. 2013;20(2):65-9. doi: 10.1038/cgt.2012.87. Epub Dec. 14, 2012.*

Tang Y, Zhang L, Yuan J, Akbulut H, Maynard J, Linton PJ, Deisseroth A. Multistep process through which adenoviral vector vaccine overcomes anergy to tumor-associated antigens. Blood. Nov. 1, 2004;104(9):2704-13. Epub Jul. 6, 2004.*

Tang Y, Maynard J, Fang XM, Zhang WW, Deisseroth A. 1128. Ad-sig-TAA/ecdCD40L Vector Prime, TAA/CD40L Protein Boost Vaccine Breaks Tolerance for Tumor Assoicated Antigens (TAA) and Suppresses Growth and Metastasis of Epithelial Neoplastic Cells. Molecular Therapy. vol. 11, Supp. 1, S435. May 2005.*

* cited by examiner

Primary Examiner — Rachel B Gill
(74) Attorney, Agent, or Firm — Jacob Frank; Glenn Snyder

(57) ABSTRACT

The present invention relates to a vaccine comprising the insertion of three genes, the TAA/ecdCD40L EA1 and CDA, driven by promoters L-plastin/cytosinedeaminase and CMV as a three gene, three transcription unit oncolytic virus as a conditionally replication competent adenoviral vector which replicates only in tumor cells. In these transcription units, the E1A gene of the adenoviral vector as well as the cytosine deaminase gene are under the control of the L-plastin promoter, while the TAA/ecdCD40L transcription unit is under control of a the CMV promoter.

3 Claims, No Drawings

TAA/ECDCD40L ONCOLYTIC VIRUS

CROSS REFERENCE TO RELATED APPLICATIONS

This application is a divisional of and claims priority to U.S. patent application Ser. No. 14/163,039 filed on Jan. 24, 2014, which claims priority to U.S. Provisional Application No. 61/757,311 filed on Jan. 28, 2013, the disclosures of which are both hereby incorporated herein by reference in their entireties.

FIELD OF THE INVENTION

The present invention relates to the field of life sciences and medicine and more particularly to cancer therapy and employment of an oncolytic adenoviral vector composition and method for treating cancer in an individual.

BACKGROUND OF THE INVENTION

Infection of Mammalian Cells by Adenoviral Vectors.

Infection of mammalian cells with adenoviral vectors involves the following phases:
a. binding
b. entry
c. uncoating
d. expression of viral genes
e. replication of DNA
f. expression of viral coat and core proteins
g. assembly of viral particles
h. cell lysis.

Replication of Adenoviral Vectors and Oncolytic Vectors.

Once the adenovirus enters a mammalian cell, the viral coat proteins unfold, releasing the viral DNA which is normally bound to a viral protein which transports the viral DNA from the cytoplasm across the nuclear membrane into the nucleus of the cell. The genes of the viral DNA are then read out into mRNA in a pre-specified fashion from viral genes which encode proteins for replication of the viral DNA and viral coat proteins. This RNA is translated into replication proteins and coat proteins. This leads to spontaneous assembly of infectious particles with a protein shell surrounding viral DNA bound to transport proteins and polymerases. The production of many infectious particles eventually results in lysis of the cell, leading to cellular death and release of thousands of infectious viral particles. With naturally occurring DNA viruses, this cycle of infection, replication and lysis of the infected cell producing infectious particles occurs in all of the cells of the body (normal cells and tumor cells).

In contrast to naturally occurring viruses, many of the "oncolytic viruses" have been genetically modified such that their replication processes occurs only in cancer cells, not in the normal cells of the body. Thus, these genetically modified viruses can infect tumor cells eventually leading to tumor cell death and the release of many infectious viral particles which have been produced inside the infected tumor cells which reside inside the tumor nodules. This process can continue until the majority of the tumor cells are destroyed.

Such vectors have been under study for several years. The strength of these vectors is that their replication machinery is genetically engineered to be specifically active in the intracellular environment of the cancer cells by making the replication of the vectors dependent on signals only present in the tumor cell. This makes the toxicity of the oncolytic virus specific for the tumor cells, thereby sparing the normal tissues of the body. This is unlike chemotherapy which damages and kills both normal and neoplastic cells.

Limitations of Oncolytic Adenoviral Vectors.

Oncolytic adenoviral vectors have the following features which limit their utility:

1. By making the replication of oncolytic vectors dependent on the regulatory environment of the tumor cells, the level of replication and total tumor cell kill is diminished.
2. Although a potent replication competent oncolytic viral vector can reduce the total body tumor burden significantly, only a fixed fraction of the total number of tumor cells die. Thus, the initial regression of the tumor cell masses which occurs immediately following chemotherapy or administration of an oncolytic vector is followed by regrowth following completion of the therapy.
3. The oncolytic adenoviral vector is not antigen specific unless specifically modified for that purpose. The invention outlined in this patent application overcomes these hurdles.
4. The oncolytic viruses, like chemotherapy and most forms of cancer treatment, kill only a fraction of the tumor cells, never 100%. This is called the fractional cell kill. The fraction or percentage of the tumor cells which are killed is a property of the type of treatment used, and the features of the particular tumor population which make a portion of the tumor cells resistant to each therapy.
5. Tumor cell populations are heterogeneous, and are composed of cells which are resistant and cells which are sensitive to each type of therapy. Following the administration of a therapy to which the majority of tumor cells are sensitive, the tumor nodule shrinks, due to death of the sensitive cells, and then regrows due to the growth of the surviving cancer cells which were resistant to therapy.

The addition of the immunotherapeutic vaccine described in the next section to the Ad-LPE1ACDA virus converts the fractional cell kill into killing of 100% of the tumor cells This conversion to a hundred percent tumor cell kill by the vaccine is conditional upon the number of tumor cells being reduced to a small number by therapies like oncolytic viruses or chemotherapy. These latter types of therapies can tackle larger number of cells than normally is the case for vaccines. As will be outlined below, for an oncolytic vector such as Ad-LPE1ACDA which also carries a TAA/ecdCD40L vaccine transcription unit (which encodes a TAA fused to the ecdCD40L) to successfully eradicate all of the tumor cells in a population, the E1ACDA transcription unit must be tumor specific and the vaccine TAA/ecdCD40L transcription unit must very strong and not necessarily tumor specific other than through the choice of the TAA to link to the ecdCD40L. That is why the TAA/ecdCD40L is driven by a CMV transcriptional promoter, and the E1ACDA transcription unit is driven by a LP promoter.

Historical Summary of the Development by Applicant of the TAA/ecdCD40L Vaccine Platform.

The TAA/ecdCD40L vaccine is based on the attachment of a fragment of a target associated antigen (TAA) fused to the extracellular domain (ecd) of the potent immunostimulatory signal CD40 ligand (CD40L). The vaccine can be administered either as a TAA/ecdCD40L protein, or as an expression vector encoding the TAA/ecdCD40L such as the adenoviral vector (Ad-sig-TAA/ecdCD40L vector), or other viral vectors, or a plasmid DNA expression vector encoding the TAA/ecdCD40L protein (1-11). The vaccine can be also administered as a vector prime followed in 7 and 21 days with sc injections of the TAA/ecdCD40L protein vaccine. This vaccine platform was developed by Applicant's laboratory (1-11) to overcome the following problems: weak immunogenicity of the target antigens, qualitative or quantitative defects of CD4 helper T cells, defective response in immunodeficient individuals including the older aged population due to diminished expression of CD40L in activated CD4 helper T cells, and/or low levels of presentation of target antigens on Class I or II MHC in dendritic cells (DCs). The CD40L is important for the expansion of antigen specific CD8 effector T cells and antigen specific B cells in response to vaccination.

Modes of Administration of TAA/ecdCD40L Vaccine.

There are four versions of this vaccine: 1. One in which the TAA/ecdCD40L transcription unit is embedded in a replication incompetent adenoviral vector (Ad-sig-TAA/ecdCD40L); 2. One in which the expression vector is used as an initial priming injection, followed by two sc injections of the TAA/ecdCD40L protein; 3. One in which the vaccine consists solely of the TAA/ecdCD40L protein; and 4. One in which the TAA/ecdCD40L is inserted into a plasmid DNA expression vector. The TAA is connected through a linker to the aminoterminal end of the ecd of the potent immunostimulatory signal CD40L (1, 3 and 5).

Impact of Attachment of TAA to CD40L.

The attachment of fragments of the TAA to the CD40L accomplishes two things: 1. the binding of the TAA/ecdCD40L protein to the CD40 receptor on the DCs as well as on the B cells and T cells activates these cells thereby promoting a potent immune response (1, 3, 5); 2. once the TAA/ecdCD40L protein is engaged on the CD40 receptor of the DC, the entire TAA/ecdCD40L protein is internalized into the DC in a way that allows Class I as well as Class II MHC presentation of the TAA (1, 5).

Activation of DCs by TAA/ecdCD40L Vaccine.

The activated TAA loaded DCs then migrate to the regional lymph nodes (1, 5) where they can activate and induce expansion of the TAA specific CD8$^+$ effector T cells. These antigen specific CD8$^+$ effector cells become increased in number in the lymph nodes (1, 5), and they then egress from the lymph nodes into the peripheral blood. The antigen specific CD8 effector T cells exit the intravascular compartment and enter into the extra-vascular sites of inflammation or infection (5, 8, 9, and 11). In addition to showing that this vaccine increases the levels of the antigen specific CD8$^+$ effector T cells in the sites of inflammation or infection (11 and 12), the Applicant's laboratory has shown that the activation and expansion of the B cells by the TAA/ecdCD40L protein increases the levels of the TAA specific antibodies (including neutralizing antibodies against viral antigens) in the serum (5, 8, 9, 11 and 12). Vaccines have been described that include an adenoviral expression vector encoding a fusion protein that includes a target associated antigen (TAA) fused to CD40 ligand (CD40L). See, e.g., U.S. Patent Application Publication US 2005-0226888 (application Ser. No. 11/009,533) titled "Methods for Generating Immunity to Antigen," filed Dec. 10, 2004.

Historical Summary of Vectors which Kill Cancer Cells Through Releasing Chemotherapy in Tumor Cells.

The Applicant's laboratory introduced a 5 fluorocytosine (5-FC) prodrug activation transcriptional unit encoding the cytosine deaminase (CDA) gene driven by the L-plastin (LP) tumor specific promoter into an adenoviral vector (2, 12-14). This vector is called Ad-LPCDA. The CDA gene catalyzes the conversion of a non-toxic prodrug, 5-FC, into the chemotherapy agent 5-fluorouracil (5-FU). They showed that the administration of the Ad-LPCDA vector to mice following intraperitoneal injection of 5-FC to test mice carrying subcutaneous deposits of tumor nodules derived from established tumor cell lines, reduced the growth of these tumor cell lines (12-14).

Applicant's laboratory had also shown that the cytotoxic effect of the Ad-LPE1ACDA vector carrying both the E1A and the CDA transgenes under the influence of the LP promoter, was greater than the vector which contains only the CDA gene prodrug activation transcription unit without the E1A gene, both in an in vitro cell line experiment as well as in an in vivo experiment in human tumor xenograft models (14). The addition of the E1A gene to the CDA gene in the LP driven transcription unit creates a chemotherapy targeting vector which is replication competent only in the tumor cells.

Applicant's laboratory then compared the action of combination chemotherapy for colon cancer with and without the administration of the Ad-LPCDA chemotherapy targeting vector following the intraperioneal injection of 5-FC (2).

The goal of creating a replication competent viral vectors is the direct killing of the target tumor cells by oncolytic effect of the virus (15-16). The goal of using the L-plastin tumor specific promoter to drive the expression of the E1A gene as well as the prodrug activation transcription unit was to increase the therapeutic effect over that seen with replication competent vectors alone or with chemotherapy targeting vectors alone. The resulting vector (Ad-LPE1ACDA) increased the antitumor effect seen with the Ad-LPCDA vector without increasing toxicity to the normal cells (12-14).

Prodrug Activation Transcription Unit Gene Therapy.

Previous reports have shown the tumor suppressive effect of adenoviral vectors carrying the CDA cDNA when used in combination with prodrug 5-FC on various tumor cell lines and in vivo models (12-18). The infectivity of normal as well as tumor cells by the adenoviral vector has represented a disadvantage for these adenoviral vectors since the expression of the therapeutic transgenes in the normal cells generates toxic side effects. In order to overcome this limitation, many groups have been focusing on tumor or tissue specific gene promoters to reduce side effects.

The L-Plastin Tumor Specific Promoter.

The plastins are a family of actin binding proteins which are responsible for functions such as cell division, intracellular trafficking, cell morphology and cell motility. There are three types: L-plastin which is found in hematopoietic cells, T-plastin, which is found in the cells of solid tissues, like in the neurons of the brain, and I-plastin, which is found in the gastrointestinal track and the kidney. L-plastin is not expressed in normal tissues (except for the leukocyte) and is expressed in all epithelial neoplastic cells. The promoter of the L-plastin gene has been used to drive expression of the cytosine deaminase gene in cancer cells (12-14). There are many other "tumor specific" transcriptional promoters (15-16).

The Cytosine Deaminase Prodrug Activation Gene.

Cytosine deaminase (CDA) is a gene found in yeast and bacterial cells, which converts the non-toxic pro-drug, 5-fluorocytosine (5-FC), into a toxic chemotherapy agent, 5-fluorouracil (5-FU). This action is known as a "prodrug activation" gene, in that it converts a non-toxic and inactive chemical, into a fully toxic and active chemical for cancer treatment. There are many other prodrug activation genes and proteins.

Use of the CDA Gene and the L-Plastin Promoter in a Replication Incompetent Adenovirus to Delivery Chemotherapy to Tumor Cells.

The Applicant's laboratory has reported experiments involving vectors carrying the tumor specific L-plastin driven genes (2, 12-14). These results showed that the replication competent viral vector can kill the tumor cell directly by oncolytic effect of the virus. The L-plastin driven CDA or CDA/E1A vectors are selectively toxic to the tumor cell lines without being toxic to the normal cells (12-14).

SUMMARY OF THE INVENTION

Applicant's invention involves insertion of the TAA/ecdCD40L (1-11) and L-plastin/cytosinedeaminase (12-14) transcription units into an oncolytic virus (15) like the conditionally replication competent adenoviral vector which replicates only in tumor cells (16). One of the novel features of the invention is the combination of three genetic elements which encode the vaccine, the chemotherapy activating gene CDA, and the replication gene E1A to make the virus replication competent. In order to make the vaccine potent, the TAA/ecdCD40L transcription unit is placed under the control of the CMV promoter, while the E1A and CDA genes are placed under the LP promoter so as to spare the normal cells from the toxic effects of viral replication by E1A and chemotherapy activation by CDA. This engineering of the timing of activation and the strength of the three different transcription units is coordinated with each other so as to maximize the tumor cell kill.

DETAILED DESCRIPTION OF THE INVENTION

In this specification, although the preferred embodiments have been described in detail, it should be understood that various changes, substitutions and alterations may be made therein without departing from the spirit and scope of the invention. Therefore, the specification is to be regarded in an illustrative rather than a restrictive sense.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in a suitable order unless otherwise indicated herein or otherwise clearly contradicted by context.

As used herein, the term "antigen" refers broadly to any antigen to which a human, mammal, bird or other animal can generate an immune response. "Antigen" as used herein refers broadly to a molecule that contains at least one antigenic determinant to which the immune response may be directed. The immune response may be cell-mediated, humoral or both.

As used herein, "antigenic determinant" refers to a single antigenic site or epitope on a complex antigenic molecule or particle, a minimal portion of a molecule that interacts with an antibody or T cell receptor. Antigenic determinants may be linear or discontinuous.

"Pharmaceutically acceptable" in the context of the present invention means a pharmaceutical composition that is generally safe, non-toxic and biologically acceptable for veterinary and human pharmaceutical use. Preferred compositions of this invention are intended for humans or animals.

The phrase "an effective amount" in reference to administering the fusion protein or an expression vector encoding that protein, is an amount that results in an increase in the immune response as measured by an increase in T cell activity or antibody production.

The fusion protein recited herein may be formulated with an adjuvant to enhance the resulting immune response. As used herein, the term "adjuvant" in the context of the instant invention means a chemical that, when administered with the expression vector or the fusion protein, enhances the immune response. An adjuvant is distinguished from a carrier protein in that the adjuvant is not chemically coupled to the antigen. Adjuvants are well known in the art and include, but not limited to, mineral oil emulsions (U.S. Pat. No. 4,608,251) such as Freund's complete or Freund's incomplete adjuvant (Freund, *Adv. Tuberc. Res.* 7:130 (1956); Calbiochem, San Diego Calif.), aluminum salts, especially aluminum hydroxide or ALHYDROGEL (approved for use in humans by the U.S. Food and Drug Administration), muramyl dipeptide (MDP) and its analogs such as [Thr$^1$]-MDP (Byersand Allison, *Vaccine* 5:223 (1987)), monophosphoryl lipid A (Johnson et al., *Rev. Infect. Dis.* 9:S512 (198)), and the like.

The term "vector" which contains a transcription unit (aka the "expression vector") as used herein refers to viral and non-viral expression vectors that when administered in vivo can enter target cells and express an encoded protein. Viral vectors suitable for delivery in vivo and expression of an exogenous protein are well known and include adenoviral vectors, adeno-associated viral vectors, retroviral vectors, vaccinia vectors, pox vectors, herpes simplex viral vectors, and the like. Viral vectors are preferably made replication defective in normal cells. For example, see U.S. Pat. Nos. 6,669,942; 6,566,128; 6,794,188; 6,110, 744; 6,133,029. The vector can be administered parenterally, such as intravascularly, intravenously, intra-arterially, intramuscularly, subcutaneously, or the like. Administration can also be orally, nasally, rectally, transdermally or aerosol inhalation. The vectors may be administered as a bolus, or slowly infused. The vector is preferably administered intratumorally, intravenously or subcutaneously, depending on the situation as is stated below in the specification.

The term "transcription unit" as it is used herein in connection with an expression vector means a stretch of DNA that is transcribed as a single, continuous mRNA strand by RNA polymerase, and includes the signals for initiation and termination of transcription. For example, in one embodiment, a transcription unit of the invention includes nucleic acid that encodes from 5' to 3' a secretory signal sequence, an influenza antigen and CD40 ligand. The transcription unit is in operable linkage with transcriptional and/or translational expression control elements such as a promoter and optionally any upstream or downstream enhancer element(s). A useful promoter/enhancer is the cytomegalovirus (CMV) immediate-early promoter/enhancer. See U.S. Pat. Nos. 5,849,522 and 6,218,140.

The term "CD40 ligand" (CD40L) as used herein refers to a full length or portion of the molecule known also as CD154 or TNF5. CD40L is a type II membrane polypeptide having a cytoplasmic domain at its N-terminus, a transmembrane region and then an extracellular domain (ecd) at its C-terminus. Unless otherwise indicated the full length CD40L is designated herein as "CD40L," "wtCD40L" or "wtTmCD40L." The nucleotide and amino acid sequence of CD40L from mouse and human is well known in the art and can be found, for example, in U.S. Pat. No. 5,962,406. Also, included within the meaning of CD40 ligand are variations in the sequence including, but not limited to, conservative amino acid changes and the like which do not alter the ability of the ligand to elicit an immune response in conjunction with the fusion protein of the invention.

The term "antibody" as used herein refers to an antibody (including a neutralizing antibody) used by the immune system to defend a cell from a target antigen or infectious body by inhibiting (or neutralizing) any function or effect, that the infectious body has biologically.

Some of the abbreviations used herein include: "Ad" (adenoviral); "sig" (signal sequence); "TAA" (target associated antigen); "ET" (epitopic target); "ecd" (extracellular domain); and "sc" (subcutaneous).

The terms "TU" means a transcription unit; "PR" means a promoter; "LP" means L-plastin; and, "CDA" means cytosine deaminiase.

The terms "strong promoter" and "weak promoter" is are respectively promoters that generates high or low levels of gene specific mRNA and protein.

The term "prodrug" means a medication that is initially administered to the body in an inactive (or less than fully active) form, and then becomes converted to its active form through the normal metabolic processes of the body.

Applicant's invention involves the following modification of a replication competent adenoviral vector:

1. The addition of a cytosine deaminase (CDA) transcription unit which is driven by the L-plastin (LP) tumor specific transcriptional promoter (2, 12-14) to a vector which contains a LP driven E1A transcription unit (Ad-LPE1ACDA) replication. That Ad-LPE1ACDA vector is then used with or without additional chemotherapy agents. The L-plastin promoter is used to drive the expression of the viral E1A gene thereby making the replication of the vector tumor specific (12-15). Following a period of 7 days after the administration of the replication competent adenovirus, during which the viral infection spreads, the harmless non-toxic prodrug, 5-fluorocytosine (5-FC) is injected intraperitoneally or intravenously. As previously described by the Applicant's laboratory (2, 12-14), the protein produced by the CDA gene when introduced into tumor cells through use of an adenoviral vector, converts 5-fluorocytosine (5-FC) prodrug into the cytotoxic drug, 5-fluorouracel (5-FU). The 5-FU concentrations achieved in this way within the tumor cells are so high that non-dividing as well as dividing cells are killed. This increases the extent of tumor cell kill.

2. Then, the TAA/ecdCD40L transcription unit is added to the Ad-LPE1ACDA adenoviral vector. In this vector, which is called Ad-LPE1ACDA[CMVTAA/ecdCD40L], the TAA/ecdCD40L transcription unit is driven by a CMV non-tumor specific promoter. As reported by the Applicant's laboratory (1, 3, 5, 6, 10 and 11), by inducing an adaptive humoral and cellular immune response against the tumor cell, the fractional cell kill can be converted into complete eradication of the tumor cell.

3. The use of the CD40L to deliver the TAA into the DC through uptake of the TAA/ecdCD40L fusion protein mediated by the CD40 receptor, the TAA eventually becomes presented on the DC on class I as well as class II MHC, thereby generating an immune response that is specific for the TAA (1, 3, 5, and 10).

4. The production of the TAA/ecdCD40L protein within the tumor cells that are infected by the Ad-LPE1ACDA vector and thereby undergoing lysis, will amplify the magnitude of the immune response induced by the TAA/ecdCD40L protein.

The combination of these elements within a single conditionally replication competent adenoviral vector creates the potential of total eradication of the tumor cell population.

Applicant's invention, which comprises a three gene, three transcription unit oncolytic adenoviral vector, has one or more of the following therapeutic goals:

1. To use the tumor specific replication competency of the adenoviral vector to reduce the total body tumor burden by several orders of magnitude;

2. To use the L-plastin-cytosine deaminase transcription unit to amplify the magnitude of the fractional cell kill over and above that possible with the replication competent adenoviral vector alone;

3. To convert the fractional cell kill (as in numbers 1 and 2 above) to a complete eradication of the tumor cell population, by adding a TAA/ecdCD40L transcription unit to the oncolytic virus.

A goal is to reduce the total body tumor burden which is high before therapy. This is accomplished by using fractional cell kill from genes which are used to create a tumor specific replication competency (oncolytic action) transcription unit and a tumor specific chemotherapy prodrug activation transcription. The TAA/ecdCD40L transcription unit is used to complete cell kill The composition of the oncolytic vector in terms of transcription units utilized is shown below:

| Transcription Unit Composition of Oncolytic Virus | | |
|---|---|---|
| LPPR E1A | LPPR CDA | CMVPR TAA/ecdCD40L |
| TU#1 | TU#2 | TU#3 |

Abbreviations:
TU = transcription unit;
PR = promoter;
LP = L-plastin;
CDA = cytosine deaminiase;
TAA = target associated antigen;
ecd = extracellular domain;
CD40L = CD 40 ligand.

As shown in Table 1 below, these three transcription units are composed of a mixture of 2 weak and 1 strong promoters, as well as 3 strong genes.

TABLE 1

Promoter and Gene Composition of Oncolytic Virus Transcription Units

| Transcription Unit | Gene | Strength of Gene | Promoter | Strength of Promoter |
|---|---|---|---|---|
| #1 | E1A | Strong | LP | Weak |
| #2 | CDA | Strong (catalytic specific activity) | LP | Weak |
| #3 | TAA/ecdCD40L | Strong | CMV | Strong |

The vector is injected intratumorally in two or three easily accessible tumor nodules. The vector is allowed to undergo several cycles of infection of tumor cells, intracellular replication and lysis due to Transcription Unit #1 (E1A gene) over a 7 day period. Note that Transcription Unit #2 is producing intracellular levels of CDA, but this does not contribute to tumor cell death until systemic injection of the prodrug 5 Fluorocytosine (5-FC), which is the non-toxic precursor or prodrug, which is catalytically converted by CDA into the chemotherapy agent 5-Fluorouracil (5-FU). Consequently, during the first week, there is replication of the oncolytic virus due to Transcription unit #1 leading to a moderate amount of cell lysis and spreading.

The effect of Transcriptional Unit #2 begins at the start of the second week, when on Day #7, 5-FC is injected intravenously, which triggers an increase in the level of tumor cell kill due to the rapid generation of intracellular levels of 5-FU in the tumor cells. Like the cell kill generated by Transcription Unit #1, this is a fractional cell kill.

The development of a TAA specific cellular and humoral immune response requires 2 weeks. Starting during the first week, there is intracellular expression of Transcription Unit #3, which leads to intracellular production of the TAA/ecdCD40L fusion protein. This fusion protein is designed to be continuously secreted or released into the extracellular space within the tumor nodules during the cycles of cell lysis of the infected tumor cells due to Transcription Units #1 and #2. The action of the TAA/ecdCD40L fusion protein takes approximately 2 weeks of expression and stimulation of the TAA specific B and CD8 Effector Cells to induce the expansion of TAA specific CD8 effector cells and TAA specific antibodies.

Initially, during the first two to four weeks after the initial injection of the oncolytic virus, the immune response is localized to the regions in which injected tumor nodules are located. However, as the immune response increases in magnitude due to the expansion of the antigen specific CD8 effector cells and antigen specific B cells, the immune response is converted from a local one surrounding the injected tumor nodules into a systemic immune response in which non-injected tumor nodules which are at sites distant from the tumor nodules initially injected become infiltrated with TAA specific CD8 effector cells and TAA specific antibodies.

This composition of strong and weak promoters, and the genes shown above and in Table 1, produces the sequence of effects of the three transcription unit on the tumor cell population shown in Table 2.

TABLE 2

Approximate Timing of the Effects of Transcription Units of the Oncolytic Virus on the Destruction of Tumor Cells in a Tumor Nodule

| Timing of Effect on Tumor Nodules (Days or Weeks After Vector Injection) | Transcription Unit | Effect on Tumor Cell Population |
| --- | --- | --- |
| Days 0-6 | #1 | Fractional Tumor Cell Kill Due to Replication of Virus |
| Days 7-14 (5-FC injection on Day 7) | #1 and #2 | Increase in Fractional Cell Kill due to Addition of Chemotherapy Induced Cell Kill to Tumor Cell Death Due to Infection and Replication of Virus |
| Days 15-28 | #3 | Local Immune Response in Injected Tumor Nodules |
| Day 29 onward | #3 | Immune Response Spreads to Un-injected Tumor Nodules and Tumor Cell Kill Converted from Fractional Cell Kill to Complete Cell Kill |

The design and composition of the transcription units introduced into the Oncolytic Virus, which is summarized in Table 1 and above is a requisite for the timed activation of the tumor cell kill and evolution of the immune response outlined in Table 2.

The classes of strong and weak tumor specific promoters for driving the respective genes as part of administering a single vector injection, are key to creating a low initial level of cell kill with spreading of the infection throughout the tumor nodules due to the action of Transcription Unit #1 during the first week after injection of the Vector. During week #2, the IV injection of the chemotherapy prodrug 5-FC results in the increase in the level of the tumor cell kill due to the catalytic action of the product of Transcription Unit #2 (CDA) on converting 5-FC into a toxic chemotherapy agent (5-FU) only in the tumor cells.

The development of an adaptive immune response against the tumor cells induced by the product of a TAA/ecdCD40L fusion protein from Transcription Unit #3 requires 2 weeks, the time required for the expansion of a sufficient number of TAA specific CD8 effector T cell lymphocytes to generate an excess of effector cells over tumor cells. At first, this result is occurring primarily within the injected tumor nodules. By the time of 4 weeks after the initial viral injection, the immune response spreads to the un-injected tumor nodules at sites distant from the injected tumor nodules, cue to migration of the CD8 effector T cell lymphocytes throughout all tumor tissues in the body, and the penetration of the tumor tissue with TAA specific antibodies.

Final Formulation of a Preferred Embodiment Vaccine.

A replication competent adenoviral vector, will be modified by introduction of the following transcriptional units:
 a. L-plastin promoter driving the cytosine deaminase gene.
 b. CMV promoter driving the expression of the TAA/ecdCD40L gene.
 c. L-plastin promoter driving the E1A gene of the adenoviral vector This viral vector will be injected on Day 1 into multiple accessible tumor nodules. On Day 7, the chemotherapy pro-drug, 5-FC, will be injected intravenously.

Criteria for Selection of Fragments of TAA for the TAA/ecdCD40L Transcription Unit.

Multiple fragments of the TAA cDNA will be attached to the ecdCD40L for introduction into a replication competent oncolytic virus will be selected on the following set of criteria:
 a. Small enough so as not to disrupt the homotrimeric structure of the ecdCD40L;
 b. Contain aminoacid domains which bind to and are recognized by Class I MHC;
 c. Contain aminoacid domains which bind to and are recognized by Class II MHC;
 d. TAA/ecdCD40L encoding transcription units, which contain multiple (at least two or more) fragments from TAA proteins to decrease the probability of immunological escape.

Advantages of the Vector System

1. Amplification of the magnitude of the tumor cell kill by adding the L-plastin/cytosine deaminase transcription unit to the L-plastin/E1A transcription unit (the Ad-LPE1ACDA vector).

2. Conversion of the fractional cell kill of chemotherapy and replication competent Ad-LPE1ACDA adenoviral vector to complete eradication of the tumor cell population through addition of the TAA/ecdCD40L transcription unit, for induction of an adaptive humoral and cellular immune response which is tumor specific.

REFERENCES

1. Zhang, L, Tang, Y, Akbulut H, Zelterman D, Linton P-J, and Deisseroth, A. An adenoviral vector cancer vaccine that delivers a tumor-associated antigen/CD40-ligand fusion protein to dendritic cells. PNAS, 100: 15101-15106, (2003).
2. Akbulut, H, Tang, Y, Maynard J, Zhang L, Pizzorno G, and Deisseroth, A. Vector targeting makes 5-fluorouracil chemotherapy less toxic and more effective in animal models of epithelial neoplasms. Clin Cancer Res 10: 7738-7746, (2004).
3. Tang, Y, Zhang, L, Yuan, J, Akbulut H, Maynard J, Linton P-J, and Deisseroth, A. Multistep process through which adenoviral vector vaccine overcomes anergy to tumor-associated antigens. Blood, 104: 2704-2713, (2004).
4. Akbulut H, Tang Y C, Akbulut K G, Maynard J, Zhang L, Deisseroth A. Antitumor immune response induced by i.t. injection of vector activated dendritic cells and chemotherapy suppresses metastatic breast cancer. Mol Cancer Ther 5:1975-1985, (2006).
5. Tang Y C, Maynard J, Akbulut H, Fang X M, Zhang W W, Xia X Q, Koziol J, Linton P-J, and Deisseroth A. Vaccine which overcomes defects acquired during aging and cancer. Journal of Immunology 177:5697-5707, (2006).
6. Tang Y, Akbulut H, Maynard J, Zhang L, Petersen L, and Deisseroth A. Vaccine strategies for cancer and infectious diseases in the elderly. Gene Therapy, Eds. Takenori Ochiai, Hideaki Shimada, and Masatoshi Tagawa, Published by Japanese Ministry of Education and Science, pp. 78-85, (2007).
7. Akbulut H, Akbulut K G, Tang Y C, Maynard J and Deisseroth A. Chemotherapy targeted to cancer tissue potentiates antigen specific immune response induced by vaccine for In vivo antigen loading and activation of dendritic cells. Molecular Therapy, 10:1753-1760, (2008).
8. Tang, Y C, Linton, P J, Thoman, M, and Deisseroth A. Symposium in Writing: Vaccine for infections and cancer. Cancer Immunology and Immunotherapy, 58: 1949-1957, (2009).
9. Han T H, Tang, Y C, Park Y H, Petersen L, Maynard J, Li P C, and Deisseroth A. Ad-sig-BcrAbl/ecdCD40L vector prime-BcrAbl/ecdCD40L protein boost vaccine for P210Bcr-Abl protein. Bone Marrow Transplantation, (2009).
10. Akbulut H, Tang Y, Akbulut K G, Maynard J, and Deisseroth A. Addition of adenoviral vector targeting of chemotherapy to the MUC-1/ecdCD40L VPPP vector prime protein boost vaccine prolongs survival of mice carrying growing subcutaneous deposits of Lewis lung cancer cells. Gene Therapy, 17: 1333-1340, (2010).
11. Deisseroth A, Tang Y, Zhang L, Akbulut H, and Habib N. TAA/ecdCD40L adenoviral prime-protein boost vaccine for cancer and infectious diseases. Cancer Gene Therapy 20: 65-69, 2013
12. Peng X Y, Won J H, Rutherford T, et al. The use of the L-plastin promoter for adenoviral-mediated, tumor-specific gene expression in ovarian and bladder cancer cell lines. Cancer Res. 61:4405-4413, (2001).
13. Zhang L, Akbulut H, Tang Y, et al. Adenoviral vectors with E1a regulated by tumor specific prooters are selectively cytolytic for breast cancer and melanoma. Mol. Therapy 6:386-393, (2002).
14. Akbulut H, Zhang L, Tang Y, Deisseroth A. The cytotoxic effect of replication competent adenoviral vectors carrying L-plastin promoter regulated E1A and cytosine deaminase genes in cancers of the breast, ovary and colon. Cancer Gene Therapy 10: 388-395, (2003).
15. Kievit E, Nyati M K, Ng E, et al. Yeast cytosine deaminase improves radiosensitization and bystander effect by 5-Fluorocytosine of human colorectal cancer xenografts. Cancer Res. 60:6649-6655, (2000).
16. Donnelly O, Errington-Mais F, Prestwich R, Harrington K, Pandha H, Vile R, and Melcher A A. Recent clinical experience with oncolytic viruses. Curr Pharm Biotechnol 13: 1834-41, (2012).
17. Alemany R, Balague C, Curiel D T. Replicative adenoviruses for cancer therapy. Nature Biotechnol. 18:723-727, (2000).
18. Hasenburg A, Tong X W, Fisher D C, et al. Adenovirus-mediated thymidine kinase gene therapy in combination with topotecan for patients with recurrent ovarian cancer: 2.5 year follow-up. Gynecol Oncol 83:549-554, (2001).
19. Deng Y, Jing Y, Campbell A E, and Gravenstein S. Age-related impaired type 1 T cell responses to influenza: reduced activation ex vivo, decreased expansion in CTL culture in vitro, and blunted response to influenza vaccination in vivo in the elderly. Journal of Immunology 172, 3437-3446, (2004).
20. Eaton S M, Burns E M, Kusser K, Randall T K and Haynes L. Age-related defects in CD4 T cells cognate helper function lead to reductions in humoral responses. J. Exp. Med. 200: 1613-1622, (2004).

The invention claimed is:

1. A method for separately administering to an individual at solely two distinct points in time yielding accelerated targeted tumor cell kill without destruction to non-tumor cells, comprising a first component and a second component of a chemical composition wherein said components are distinct from one another,
   a) the first component, a tumor specific replication competent oncolytic adenoviral nucleic acid backbone expression vector, comprising:
      i) a first Ad-LPE1A transcription unit which comprises an L-plastin like tumor specific promoter driving an E1A like gene which stimulates viral replication, ii) a second transcription unit Ad-LPCDA comprising a gene encoding for cytosine deaminase (CDA) which is driven by a second L-plastin like tumor specific promoter for generating a CDA gene product, and iii) a third transcription unit Ad-CMV TAA/ecdCD40L encoding a fusion protein comprising a tumor associated antigen linked to the extracellular domain of a CD40 ligand (TAA/ecdCD40L) which is driven by a cytomegalovirus (CMV) tumor non-specific promoter, wherein said three transcription units are contained within said adenoviral expression vector and each of said three transcription units is chemically independent and distinct from the other two transcription units,
   b) the second component, a prodrug, comprising a 5-fluorocytosine (5-FC) prodrug adapted to be catalytically converted by the CDA gene product into the 5-fluorouracil (5-FU) chemotherapy agent, where said prodrug is not encoded from the expression vector transcription units, and
   c) wherein the first component is administered on day one of week one where the expression vector first component is to be injected intratumorally into an individual, and the second component is singularly administered on day one of week two from the time of said injection of said expression vector where said second component is to be injected intravenously into the individual, and
   d) wherein the effect of said solely two distinct timed administrations of the compositions of said first component and said second component, generates a systemic adaptive immune response in the individual yielding accelerated targeted tumor cell kill without destruction to non-tumor cells.

2. A method according to claim 1, wherein said expression vector is configured to be replication competent to replicate only in cancer cells.

3. A method according to claim 1, wherein said expression vector is replication competent and said L-plastin like tumor specific promoter is of a first strength in driving first levels of gene specific mRNA and protein, and said CMV tumor non-specific promoter is of a second strength greater than the first strength to generate second levels of gene specific mRNA and protein higher than the first levels.

* * * * *